United States Patent [19]
Stüwe et al.

[11] Patent Number: 5,969,205
[45] Date of Patent: Oct. 19, 1999

[54] PROCESS FOR PREPARING $C_4$–$C_6$–ALKENES HAVING AN INTERNAL DOUBLE BOND COMPRISING RECYCLING A PORTION OF A PRODUCT STREAM

[75] Inventors: Arnd Stüwe, Leverkusen; Jörg-Uwe Michel; Matthias Baum, both of Dormagen; Franz Kaledat, Neuss, all of Germany

[73] Assignee: EC Erdolchemie GmbH, Cologne, Germany

[21] Appl. No.: 09/137,860

[22] Filed: Aug. 21, 1998

[30] Foreign Application Priority Data

Aug. 26, 1997 [DE] Germany ............................ 197 37 019

[51] Int. Cl.⁶ ......................................... C07C 5/23
[52] U.S. Cl. .......................... 585/664; 585/665; 585/666; 585/667; 585/668; 585/669; 585/670
[58] Field of Search .................................. 585/664–665, 585/670

[56] References Cited

U.S. PATENT DOCUMENTS

| | | | |
|---|---|---|---|
| 3,531,545 | 9/1970 | Garner et al. ........................ | 260/683.2 |
| 4,132,745 | 1/1979 | Amigues et al. ..................... | 260/683.2 |
| 4,392,002 | 7/1983 | Cosyns et al. ........................ | 585/329 |
| 4,435,609 | 3/1984 | Gschwendtner ..................... | 585/664 |
| 4,849,576 | 7/1989 | Nowack et al. ...................... | 585/670 |
| 5,008,466 | 4/1991 | Schleppinghoff et al. ........... | 568/697 |
| 5,177,281 | 1/1993 | Haag et al. .......................... | 585/664 |

FOREIGN PATENT DOCUMENTS 2 438 084  5/1981  France .

Primary Examiner—Walter D. Griffin
Assistant Examiner—In Suk Bullock
Attorney, Agent, or Firm—Connolly Bove Lodge & Hutz LLP

[57] ABSTRACT

$C_4$–$C_6$-alkenes having an internal double bond can be produced by hydroisomerization of $C_4$–$C_6$-alkenes having a terminal double bond in the presence of $H_2$ on a catalyst having a content of a noble metal of group VIII of the Periodic Table of the Elements (Mendeleev), if $C_4$–$C_6$-alkenes having a terminal double bond are fed into a hydroisomerization reactor after preheating, as such or in a mixture with other hydrocarbons, and the reaction product is divided into a work-up stream and a recycle stream. The recycle stream is recycled to the inlet of the hydroisomerization reactor and is used there as feed together with the $C_4$–$C_6$-alkenes having a terminal double bond or with the hydrocarbon stream comprising the $C_4$–$C_6$-alkenes having a terminal double bond and with the $H_2$.

11 Claims, 1 Drawing Sheet

PROCESS FOR PREPARING $C_4$—$C_6$—ALKENES HAVING AN INTERNAL DOUBLE BOND COMPRISING RECYCLING A PORTION OF A PRODUCT STREAM

BACKGROUND OF THE INVENTION

1. Field of the Invention

The present invention relates to a process for preparing $C_4$–$C_6$-alkenes having an internal double bond by hydroisomerization of $C_4$–$C_6$-alkenes having a terminal double bond, in which the product stream exiting from the reactor is divided into a work-up stream and a recycle stream, and the recycle stream is recycled to the reactor inlet, where, together with the $C_4$–$C_6$-alkenes having a terminal double bond and the $H_2$, it forms the feed for the reactor. The process serves especially for converting 1-butene into 2-butene.

2. Description of the Related Art

Alkenes having an internal double bond, for example 2-butene, are sought-after alkylating agents for alkylating n-alkanes and/or i-alkanes, valuable motor fuels ("alkylate gasoline") being produced. Such alkylates of olefins having an internal double bond produce, in the motor fuel sector, better properties than alkylates of olefins having a terminal double bond. Thus, for example, n-1-butene with n-butane/i-butane produces an alkylate gasoline having a research octane rating ROR of 92.5, whereas the corresponding alkylate of 2-butene has an ROR of 98.5 (Oil and Gas Journal 8 (1971), 60). The shift of terminal double bonds to an internal position of the olefin therefore represents an important step in the production of high-octane gasoline.

The conversion, for example, of 1-butene to 2-butene has long been carried out as a so-called hydroisomerization in the presence of hydrogen on a catalyst suitable for the hydrogenation. Thus U.S. Pat. No. 3,531,545 discloses using for this purpose a catalyst having a content of Pd or Pt on $SiO_2$ or $Al_2O_3$ as support, which, however, to avoid the undesirable overhydrogenation, is damped in its activity using sulfur compounds. However, as a consequence of this, the hydroisomerization must be carried out at a temperature of up to 155° C. However, the thermodynamic equilibrium is more on the side of 1-butene at higher temperatures, so that lower hydroisomerization yields can be achieved at higher temperatures. According to FR 2,438,084, an increase in selectivity of a $Pd/Al_2O_3$ catalyst can also be induced, apart from a treatment with sulfur compounds, by a treatment with ammonia or carbon monoxide. A further variant of the increase in selectivity is described in U.S. Pat. No. 4,132,745 in which a $Pd/Al_2O_3$ catalyst is treated with hydrogen sulfide and then with hydrogen; at 80 to 100° C., using such a catalyst, a hydroisomerization is carried out in which the accompanying butadiene is substantially eliminated by hydrogenation, but a considerable portion of butene is also undesirably hydrogenated to give the saturated butane. DE-A 31 40 573 describes a hydroisomerization of 1-butene to 2-butene on a catalyst containing 0.3% Pd on high-purity $Al_2O_3$, which is performed subsequently to the oligomerization of i-butene and in the presence of the oligomer. The isomerization is carried out at 120° C. and at a molar ratio of hydrogen to hydrocarbons of 0.5. EP-A 338 309 discloses that alkenes having a terminal double bond can be isomerized to form alkenes having an internal double bond if the catalyst used is a macroporous or gel-form cation exchanger in the H+ form, which contains 0.001 to 10 g of a metal of subgroup VIII of the Periodic Table of the Elements (Mendeleev) per liter of cation exchanger.

SUMMARY OF THE INVENTION

It has now been found that the degree of isomerization of $C_4$–$C_6$-alkenes having a terminal double bond to $C_4$–$C_6$-alkenes having an internal double bond is increased in in the direction of the thermodynamic equilibrium if the product stream exiting from the reactor is divided into a work-up stream and a recycle stream and the recycle stream is recycled to the feed or the reactor inlet. This recycled part-stream can, if appropriate, be cooled. The recycling initially brings an increased mass flow rate through the hydroisomerization reactor and a dilution of the $C_4$–$C_6$-alkenes having a terminal double bond to be isomerized. These features cause a decrease in the space-time yield and thus the results obtain would not have been expected. However, the increase in the mass flow rate is at the same time accompanied by improved solubility of the hydrogen used and also permits the possibility of a decrease in temperature. These last-mentioned features (improved $H_2$ solubility, lower temperature), however, would have permitted those skilled in the art to expect, at best, an improvement in the hydroisomerization result by about 0.5% in the direction of the thermodynamic equilibrium. However, surprisingly, in the process according to the invention improvements by 5 to 7% points in the direction of the thermodynamic equilibrium are achieved.

The invention relates to a process for preparing $C_4$–C6-alkenes having an internal double bond by hydroisomerization of $C_4$–$C_6$-alkenes having a terminal double bond in the presence of hydrogen on a catalyst having a content of a noble metal of group VIII of the Periodic Table of the Elements (Mendeleev), which comprises the process steps a) introducing a feed of heated $C_4$–$C_6$-alkenes having a terminal double bond, hydrogen and a recycle stream having a temperature of 15 to 60° C. into a reactor which is charged with the noble-metal containing catalyst, b) isomerizing the $C_4$–$C_6$-alkenes having a terminal double bond present in the feed at the catalyst in the reactor at an LHSV of 1 to 20 $h^{-1}$, 15 to 120° C. and a pressure at which the C4–$C_6$-alkenes having a terminal double bond and the recycle stream are present in the liquid phase, for substantial establishment of the thermodynamic equilibrium between $C_4$–$C_6$-alkenes having a terminal double bond and $C_4$–$C_6$-alkenes having an internal double bond, c) dividing the product stream exiting from the reactor into a work-up stream and a recycle stream which in the steady state is 0.1 to 10 times the work-up stream, d) recycling the recycle stream to step a) and e) isolating the $C_4$–$C_6$-alkenes having an internal double bond from the work-up stream.

DETAILED DESCRIPTION OF THE INVENTION

Figure 1:
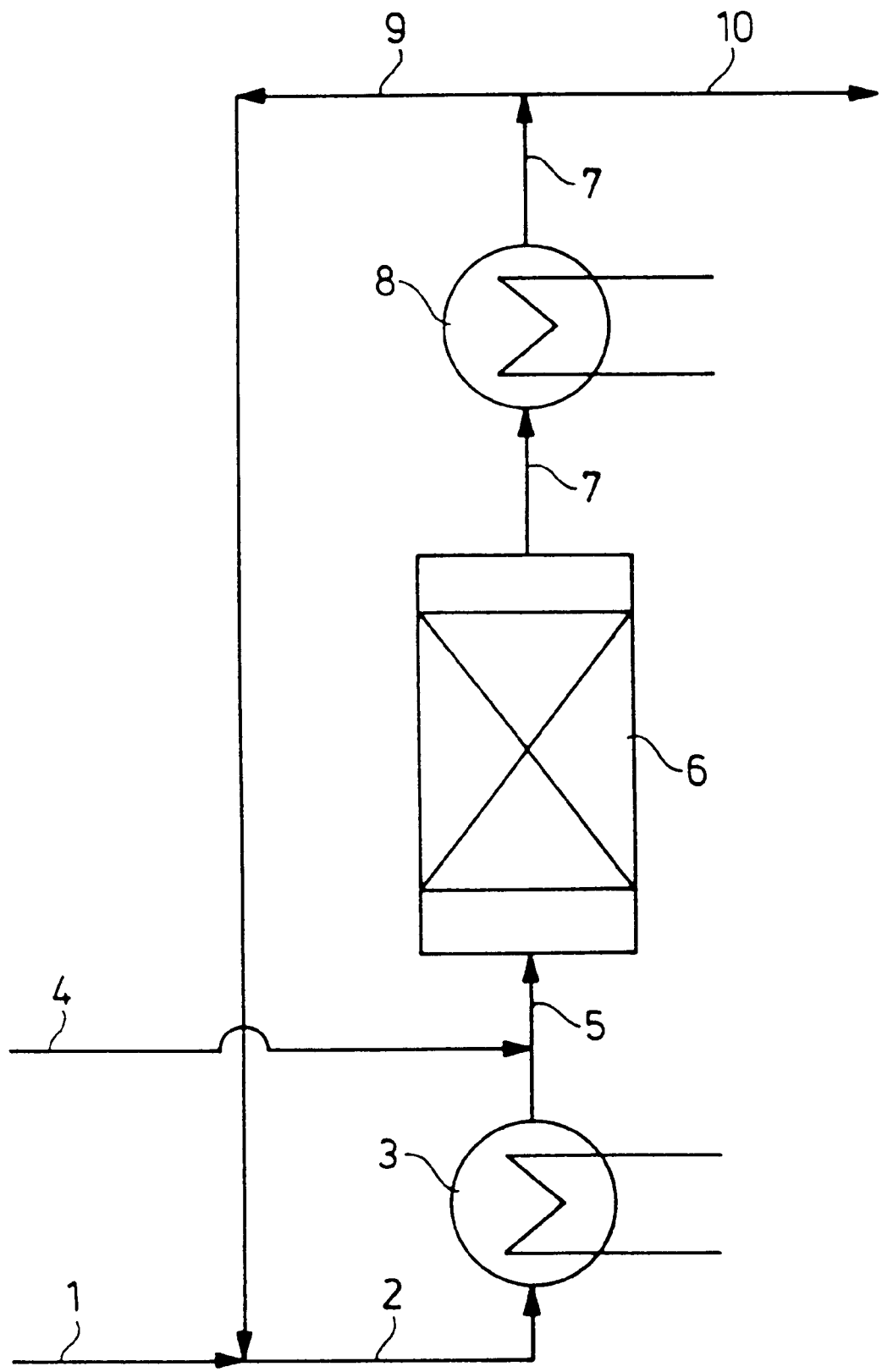

Between $C_4$–$C_6$-alkenes having a terminal double bond and $C_4$–$C_6$-alkenes having an internal double bond, there is a thermodynamic equilibrium which is displaced at high temperatures strongly toward the side of the $C_4$–$C_6$-alkenes having a terminal double bond and at low temperatures toward the side of the $C_4$–$C_6$-alkenes having an internal double bond. In the effluent of a cracker (steam cracker or catalytic cracker) there is therefore constantly a high proportion of $C_4$–$C_6$-alkenes having a terminal double bond, for example of 1-butene, compared with the proportion of $C_4$–$C_6$-alkenes having an internal double bond, for example 2-butene, which is frozen by quenching this effluent and does not correspond to the actual requirement of the two individual isomers.

The process according to the invention thus permits the preparation of 2-butene from 1-butene, of 2-pentene from 1-pentene and of a mixture of 2-hexene and 3-hexene from 1-hexene; the preparation of 2-butene from 1-butene, which is described as an example below, is of particular importance in this case. Those skilled in the art can apply this description in a simple manner to the analogous preparation of 2-pentene or 2-hexene/3-hexene.

In the process according to the invention, the 1-butene can, for example, be used as such or as a mixture with other hydrocarbons. The use of 1-butene in the form of the industrially available hydrocarbon mixtures is particularly important. Such mixtures comprise, in addition to the 1-butene, further saturated, monounsaturated and diunsaturated hydrocarbons and, if appropriate, small amounts of acetylenically unsaturated hydrocarbons having, for example, 1 to 6 carbon atoms, in the case of the $C_5$-/$C_6$-alkenes also up to 8 carbon atoms. Mixtures of this width in carbon number range can be produced in a crude distillation of a cracker effluent and used according to the invention. However, of more interest than a crude distillation fraction of this type is the use of a more precise distillation fraction which, for example, essentially comprises $C_4$-hydrocarbons, for instance in addition to 1-butene, n-butane, i-butane, cis-2-butene, trans-2-butene, i-butene, butadiene, vinylacetylene and minor amounts of hydrocarbons of the adjoining $C_3$- and $C_5$-ranges. Particularly preferably, instead of a crude $C_4$-distillation fraction of this type, a so-called raffinate 1 is used which has substantially been freed from butadiene by suitable measures (for example by extraction). A typical composition of a raffinate 1 from a steam cracker is as follows:

| Raffinate 1 component | | |
|---|---|---|
| n-butane | % | 10–20 |
| i-butane | % | 0,5–1 |
| 1-butene | % | 20–25 |
| 2-butene (cis) | % | 5–8 |
| 2-butene (trans) | % | 8–11 |
| i-butene | % | 38–45 |
| butadiene | % | 0.1–0.3 |
| $C_3$ hydrocarbon | % | 0–1 |
| $C_5$ hydrocarbon | % | 0–1 |

As an alternative to this, a so-called raffinate 2 can also be used which is obtained by catalytic conversion and thus removal of the i-butene present in the raffinate 1. Obviously, in general, the corresponding mass streams having contents of 1-pentene and/or 1-hexene can be used. Finally, it is also possible to use a mass stream which comprises 1-butene and 1-pentene or all $C_4$–$C_6$-alkenes having a terminal double bond.

Hydrogen can be used in the process according to the invention in pure or technical-grade form. Economically advantageously, use can be made of, for example, a hydrogen which is produced in petrochemical plants and is associated with methane and/or nitrogen, or use can be made of an $H_2$-containing residual gas from petrochemical plants. The $H_2$ content in such technical-grade or pure hydrogens is 70 to 100% by volume of $H_2$, in residual gases frequently about 80 to 90% by volume of $H_2$. The hydrogen is not consumed in the hydroisomerization, but acts catalytically. Therefore, its quantity is in principle optional, for example 0.5 to 20 liters at S.T.P. (1 S.T.P.) per 1 of 1-butene, preferably 1 to 15 l S.T.P., particularly preferably 1 to 5 l S.T.P. per 1 of 1-butene. In the upper part of said range, however, one must expect a marked hydrogenation of the 1-butene which is particularly susceptible to hydrogenations, that is containing the terminal double bond (generally $C_4$–$C_6$-1-alkene). In the lower part of said range, lower reaction rates must be expected, in particular if the process is to be carried out in the range of low temperatures and in the range of higher LHSV (liquid hourly space velocity) values. It is therefore particularly advantageous according to the invention if, owing to the increase of the mass flow rate due to the recycle stream, the region of low $H_2$ rates can be employed. A further advantage of the process according to the invention is that the hydrogenation-susceptible butadiene (generally $C_4$–$C_6$-alkadiene), if it is present in the feed, is hydrogenated to below the detectability limit to 1-butene (generally $C_4$–$C_6$-1-alkene) which, in the context of the hydroisomerization according to the invention, can be converted to 2-butene (generally $C_4$–$C_6$-alkene having an internal double bond). However, owing to the desired hydrogenation of, for example, butadiene, and as a consequence of a hydrogenation of 1-butene which cannot always be completely avoided, in addition to the pure catalytic action of $H_2$, there is a certain consumption of $H_2$ which must be replaced. Otherwise, the $H_2$ produced during the work-up can be recycled again.

As noble metals of group VIII of the Periodic Table of the Elements (Mendeleev) which have a hydrogenation activity and can be used according to the invention, Ru, Rh, Pd, Ir and Pt may be mentioned. Of these, preference is given to Pd and Pt, but in particular Pd. The noble metals are always used in a dispersed form on a support. Suitable supports are, for example, inorganic materials, such as $Al_2O_3$, $SiO_2$ or activated carbons, and other supports known for these purposes by those skilled in the art. The amount of the noble metal on such inorganic supports is typically 0.001 to 10% by weight, typically 0.1 to 5% by weight, based on the total weight of the support including noble metal. However, supports can also be, for example, of organic nature, such as cation exchangers based on phenol-formaldehyde resins having introduced sulfonic acid groups, or styrene-divinylbenzene resins, likewise having introduced sulfonic acid groups.

To carry out the process according to the invention, a reactor is used which is charged with the abovedescribed catalyst which comprises a noble metal of group VIII of the Periodic Table of the Elements. This reactor can, for example, be designed as a shaft reactor, as a tubular reactor, as a tube-bundle reactor or in another suitable manner.

Into this reactor, there is introduced a feed which consists, for example, of 1-butene, hydrogen and the abovementioned recycle stream. The 1-butene in this case is used as such or in the form of one of the abovedescribed hydrocarbon mixtures. The 1-butene, as such or in the form of one of the abovementioned hydrocarbon mixtures, is brought, prior to the introduction into the reactor, to a temperature of 15 to 60° C., preferably from 15 to 40° C., particularly preferably 15 to 30° C. In the same manner, the hydrogen likewise associated with the feed is heated. The heating of the $H_2$ can take place in this case jointly with the 1-butene or a hydrocarbon stream comprising the 1-butene. Separate heating of the $H_2$ can be omitted if the $H_2$ is already at a suitable temperature. In a similar manner, the recycle stream is heated, in which case, likewise before the heating, it can be mixed with the 1-butene or a hydrocarbon stream comprising the 1-butene and/or with the $H_2$. A separate heating of the recycle stream can, as already described for $H_2$, be omitted if the recycle stream is already at a suitable temperature. In principle, the constituents of the feed to be introduced can be introduced separately at different places of the reactor. However, it is expedient to mix the constituents of the feed in advance and then introduce them into the reactor.

The feed introduced into the reactor of, for example, 1-butene, $H_2$ and the recycle stream is hydroisomerized in the reactor at 15 to 120° C., preferably 20 to 80° C., particularly preferably 20 to 60° C. The reaction mixture in this case, except for incompletely dissolved components of $H_2$, is in the liquid phase. The reaction mixture is passed over the catalyst at an LHSV (liquid hourly space velocity) of 1 to 20 $h^{-1}$ (liter of liquid reaction mixture per liter of catalyst per hour), preferably 3 to 15 $h^{-1}$, particularly preferably 5 to 12 $h^{-1}$. To maintain the liquid phase, as described above, a suitable pressure is maintained in the reactor. This pressure is generally the autogenous pressure which is established inherently. For example, a range of 5 to 30 bar, preferably 8 to 20 bar, may be mentioned. Under these reaction conditions, the thermodynamic equilibrium, for example between 1-butene and 2-butene, is established. In the abovementioned manner, this thermodynamic equilibrium is, at lower temperature, more toward the side of the desired 2-butene; it is therefore desirable and possible according to the invention to set a reaction temperature as low as possible, a sufficient hydroisomerization rate needing to remain ensured, however.

The product stream exiting from the reactor is divided into a work-up stream and a recycle stream. The recycle stream in this case is 0.1 to 10 times the work-up stream, preferably 0.1 to 4 times, particularly preferably 0.1 to 2 times the work-up stream. The recycle stream is recycled to the inlet of the reactor and is there introduced into the reactor in process step a) together with, or separately from, for example, the 1-butene and the hydrogen as feed. The recycle stream can in this case, as likewise has already been described above, be heated separately or together with 1-butene and/or hydrogen. It can be useful to bring the product stream exiting from the reactor to a suitable temperature in a heat exchanger upstream of the division into a work-up stream and a recycle stream. However, it can be equally useful not to bring the product stream exiting from the reactor to a suitable temperature until after its division; in this case the recycle stream may already have a temperature suitable for its introduction into the reactor, so that it no longer needs to be heated separately. Similarly, the work-up stream need not be brought, in a heat exchanger, to a temperature which is suitable for the subsequent work-up, until after the division of the product stream exiting from the reactor. The product stream, which then substantially approximates to the thermodynamic equilibrium, for example between 2-butene and 1-butene, is worked up by methods known to those skilled in the art, for example by distillation or oligomerization.

One of the possible embodiments of the process according to the invention may be represented on the basis of the accompanying FIG. 1 and described with reference to the example of the conversion of 1-butene to 2-butene. In FIG. 1, (1) denotes 1-butene or a hydrocarbon stream comprising the 1-butene which is not yet in thermodynamic equilibrium between 2-butene and 1-butene; the stream (1) is combined in an embodiment which is possible according to the invention and represented in FIG. 1, with a recycle stream (9) and set to the desired temperature as a combined stream (2) via a heat exchanger (3); after the heating, hydrogen in the intended amount is added to this combined stream, for example, via the line (4) and the combined stream is introduced into the reactor (6) as combined feed via the line (5); the product stream hydroisomerized (6) runs via the line (7) via a heat exchanger (8), for example, and is subsequently divided into the work-up stream (10) and the recycle stream (9), to which 1-butene is admixed.

ILLUSTRATIVE EXAMPLES

Examples 1–6

In an apparatus as in FIG. 1, a 1-butene-containing feed was reacted under the conditions specified in the table below.

| Example | 1 | 2 | 3 | 4 | 5 | 6 |
|---|---|---|---|---|---|---|
| Pressure (bar) | 17 | 14 | 14 | 14 | 14 | 14 |
| $H_2$ (1 S.T.P./1 of total feed) | 7 | 4 | 3 | 8 | 5 | 6 |
| LHSV (overall) | 8 | 9 | 9 | 8 | 8 | 8 |
| Recirculation (%) | 0 | 15 | 30 | 17 | 17 | 0 |
| Inlet temperature (° C.) | 20 | 19 | 19 | 16 | 16 | 16 |
| Outlet temperature (° C.) | 66 | 51 | 46 | 68 | 49 | 52 |
| Inlet 1-butene (% by weight) | 23.6 | 20.9 | 17.9 | 21.4 | 21.4 | 25.2 |
| Outlet 1-butene (% by weight) | 8.1 | 3.5 | 2.2 | 4 | 4.5 | 9 |
| Hydrogenation of butenes (%) | 4.5 | 2.3 | 1.7 | 5.3 | 3.2 | 3.6 |
| Hydrogenation of butadiene (%) | 100 | 100 | 100 | 100 | 100 | 100 |

Explanations to the table:

Examples 1 and 6: without recirculation procedure (24–25% 1-butene)

Examples 2, 4 and 5: with 15 to 17% recirculation (1-butene dilution)

Example 3: with 30% recirculation (1-butene dilution)

Comparison of Examples 1, 2 and 3 (advantages with increasing the recirculation):
- improvement of isomerization (low 1-butene content in the outlet)
- use of lower $H_2$ rates by minimizing side reactions (here: hydrogenation of butenes)
- lower temperature increase in the reactor Comparison of Examples 2, 4 and 5 (advantages with the use of lower $H_2$ rates at a constant recirculation):
- lower temperatures at the reactor outlet
- improvement of the isomerization at low temperatures by more favorable position of the thermodynamic equilibrium
- lower losses of butenes due to hydrogenation Comparison of Examples 1 and 6:

Without the recirculation procedure, even under otherwise favorable conditions, isomerization is still insufficient.

We claim:

1. A process for preparing $C_4$–$C_6$-alkenes having an internal double bond by hydroisomerization of $C_4$–$C_6$-alkenes having a terminal double bond in the presence of hydrogen and a catalyst comprising a noble metal of group VIII of the Periodic Table of the Elements (Mendeleev), which comprises:

a) introducing a feed of heated $C_4$–C6-alkenes having a terminal double bond, $H_2$ and a recycle stream having a temperature of 15 to 60° C. into a reactor which is charged with the noble-metal containing catalyst, b) isomerizing the $C_4$–$C_6$-alkenes having a terminal double bond present in the feed in the reactor at an LHSV of 1 to 20 $h^{-1}$, 15 to 120° C. and a pressure at which the $C_4$–$C_6$-alkenes having a terminal double bond and the recycle stream are present in the liquid phase, c) dividing the product stream exiting from the reactor into a work-up stream and a recycle stream which in the steady state is 0.1 to 10 times the work-up stream, d) recycling the recycle stream to step a) and e) isolating $C_4$–C6-alkenes having an internal double bond from the work-up stream.

2. The process of claim 1, wherein the $C_4$–$C_6$ alkenes further comprises saturated, monounsaturated and diunsaturated hydrocarbons having 1 to 8 carbon atoms.

3. The process of claim 1, wherein $H_2$ rate is 0.5 to 20 l S.T.P./l of 1-butene.

4. The process of claim 1, wherein the $C_4$–$C_6$-alkenes are heated to a temperature of 16 to 40° C. and the reaction temperature is 20 to 80° C.

5. The process of claim 1, wherein the pressure in the reactor is 5 to 30 bar.

6. The process of claim 1, wherein the LHSV is 3 to 15 $h^{-1}$.

7. The process of claim 1, wherein the recycle stream is 0.1 to 4 times the work-up stream.

8. The process of claim 1, wherein the noble metal used is palladium or platinum.

9. The process of claim 1, wherein the noble metal is present on an $Al_2O_3$ support.

10. The process of claim 1, wherein the $C_4$–$C_6$-alkene is 1-butene.

11. The process of claim 10, wherein the 1-butene is in the form of a $C_4$-distillation fraction.

* * * * *